United States Patent
Ahn et al.

(10) Patent No.: US 12,251,195 B2
(45) Date of Patent: Mar. 18, 2025

(54) CORE BODY TEMPERATURE MEASUREMENT DEVICE HAVING THERMISTOR-PROTRUDING STRUCTURE

(71) Applicant: OSONG MEDICAL INNOVATION FOUNDATION, Cheongju-si (KR)

(72) Inventors: Jin Woo Ahn, Cheongju-si (KR); Young Hoon Roh, Seoul (KR); Ha Chul Jung, Cheongju-si (KR); Young Jin Kim, Cheongju-si (KR); Kang Moo Lee, Sejong-si (KR); Seung A Lee, Seoul (KR); Da Hye Kwon, Bucheon-si (KR); Ha Na Park, Cheongju-si (KR); A Hee Kim, Cheongju-si (KR); Song Woo Yoon, Cheongju-si (KR); Won Jung Choi, Cheongju-si (KR)

(73) Assignee: OSONG MEDICAL INNOVATION FOUNDATION, Cheongju-si (KR)

( * ) Notice: Subject to any disclaimer, the term of this patent is extended or adjusted under 35 U.S.C. 154(b) by 730 days.

(21) Appl. No.: 17/293,247

(22) PCT Filed: Nov. 27, 2018

(86) PCT No.: PCT/KR2018/014691
§ 371 (c)(1),
(2) Date: May 12, 2021

(87) PCT Pub. No.: WO2020/111289
PCT Pub. Date: Jun. 4, 2020

(65) Prior Publication Data
US 2022/0000369 A1   Jan. 6, 2022

(30) Foreign Application Priority Data

Nov. 26, 2018 (KR) .................. 10-2018-0147053

(51) Int. Cl.
*A61B 5/01* (2006.01)
*A61B 5/00* (2006.01)

(52) U.S. Cl.
CPC .............. *A61B 5/01* (2013.01); *A61B 5/6817* (2013.01); *A61B 2562/16* (2013.01)

(58) Field of Classification Search
None
See application file for complete search history.

(56) References Cited

U.S. PATENT DOCUMENTS

| 2005/0209516 | A1* | 9/2005 | Fraden | A61B 5/14552 |
| | | | | 600/323 |
| 2007/0135717 | A1 | 6/2007 | Uenishi et al. | |
| 2012/0217087 | A1* | 8/2012 | Ambrose | H04R 1/1016 |
| | | | | 181/130 |

FOREIGN PATENT DOCUMENTS

| CA | 2069625 B | 8/1996 |
| JP | 03-051410 B2 | 6/1989 |

(Continued)

OTHER PUBLICATIONS

International search report issued on Aug. 26, 2019.
European search report issued on Jun. 29, 2022.

*Primary Examiner* — Aurelie H Tu
(74) *Attorney, Agent, or Firm* — LEEPI

(57) ABSTRACT

A core body temperature measurement device includes a body and an operation unit. The body is fixed to an ear canal of user. The operation unit is combined with a front side of the body, and is configured to be exposed to the ear canal or to be concealed inside, and has a sensor part. the sensor part measures a core body temperature of user when the operation unit is exposed to the ear canal.

5 Claims, 5 Drawing Sheets

(56) References Cited

FOREIGN PATENT DOCUMENTS

| | | |
|---|---:|---:|
| JP | 3052379 B2 | 12/1990 |
| JP | 08-112259 A | 10/1994 |
| JP | 2016-118402 A | 6/2016 |
| KR | 10-1779837 B1 | 9/2017 |
| KR | 10-1804374 B1 | 12/2017 |
| WO | 2017203251 A1 | 11/2017 |

* cited by examiner

CORE BODY TEMPERATURE MEASUREMENT DEVICE HAVING THERMISTOR-PROTRUDING STRUCTURE

BACKGROUND

1. Field of Disclosure

The present disclosure of invention relates to a core body temperature measurement device, and more specifically the present invention relates to a core body temperature measurement device having a thermistor-protruded structure, capable of measuring a core body temperature.

2. Description of Related Technology

A core body temperature means a temperature of an inside of human body, and a core body temperature measurement device for measuring the core body temperature has been developed variously and widely used.

Conventionally, in the core body temperature, as disclosed by Korean Patent No. 10-1779837, the device is inserted into an ear to measure a temperature of drumhead. Here, a temperature difference between first and second sensors insulated with each other is used to obtain the core body temperature.

In addition, as disclosed by Korean Patent No. 10-1804374, the device is inserted into the ear and the core body temperature is measured using an infrared ray.

However, in the conventional core body temperature device, a sensor is continuously exposed inside of an ear canal, and thus the user may feel uncomfortable or a foreign body. In addition, the exposed portion may be damaged or polluted to be malfunctioned.

Related prior arts are Korean Patent No. 10-1779837 and Korean Patent No. 10-1804374.

SUMMARY

The present invention is developed to solve the above-mentioned problems of the related arts. The present invention provides a temperature measurement device having a thermistor-protruded structure, capable of increasing reliability of the results, being disinfected, and increasing convenience of user.

According to an example embodiment, core body temperature measurement device includes a body and an operation unit. The body is fixed to an ear canal of user. The operation unit is combined with a front side of the body, and is configured to be exposed to the ear canal or to be concealed inside, and has a sensor part. the sensor part measures a core body temperature of user when the operation unit is exposed to the ear canal.

In an example, the operation unit may include a cover frame configured to form an outer shape of the operation unit, a rotation part disposed inside of the cover frame and configured to receive a driving force to be rotated, and first and second moving parts combined with both sides of the rotation part respectively and configured to move along an inner side of the cover frame when the rotation part is rotated.

In an example, the sensor part may be fixed to the second moving part. The sensor part may be exposed outside of the cover frame to measure the core body temperature, or may be concealed inside of the cover frame, according to the movement of the second moving part.

In an example, the operation unit may further include a disinfection part configured to disinfect the sensor part, when the sensor part is concealed inside of the cover frame.

In an example, the sensor part may include an extending portion fixed to the second moving part and extending along a direction, and a sensor disposed at an end of the extending portion, to measure the core body temperature.

In an example, the operation unit may include a cover part fixed to the first moving part, and configured to open or close an opening portion of the cover frame through which the senor part is exposed.

In an example, the operation unit may further include a guide part. The guide part may be tightly attached with the cover part and a first end of the guide part may be combined with the rotation part, to open or close the opening portion of the cover frame with the cover part. The guide part may form a guide in which the sensor part moves with exposed or concealed.

According to the present example embodiments, the sensor part is selectively exposed to the ear canal or is concealed inside, and the core-temperature is measured when exposed, and thus the sensor may be prevented from being infected or the user may feel less inconvenience or less foreign body since the sensor part is not always disposed in the ear canal.

An operation structure or motion for exposing or concealing the sensor part, is merely performed by the clockwise or counterclockwise rotation of the rotation part, and thus the operation structure or motion is very simple, so that the sensor part may be easily driven in a relatively narrow space of the ear canal. Thus, usability and productivity may be increased.

Here, the first and second moving parts are combined with the rotation part via a gear combination, so that the operation may be stably controlled with a stable combination state.

The cover frame is closed or open by the cover part, and at the same time, the exposure of the sensor part through the opening portion is performed with the movement of the cover frame, so that the control and the driving may be more simplified.

In addition, the sensor part is guided by the guide part, so that the exposure and the concealment of the sensor part may be performed with more increased reliability.

In addition, the sensor part is disinfected by the disinfection part when the sensor part is concealed, so that the sensor part which is disposed at the ear canal to be easily infected is prevented from being infected. Further, during the disinfection, the noxious light or material is prevented from being exposed to the user by the cover frame, so that the sensor part may be maintained more cleanly and may measure the core body temperature more correctly.

Figure 1:
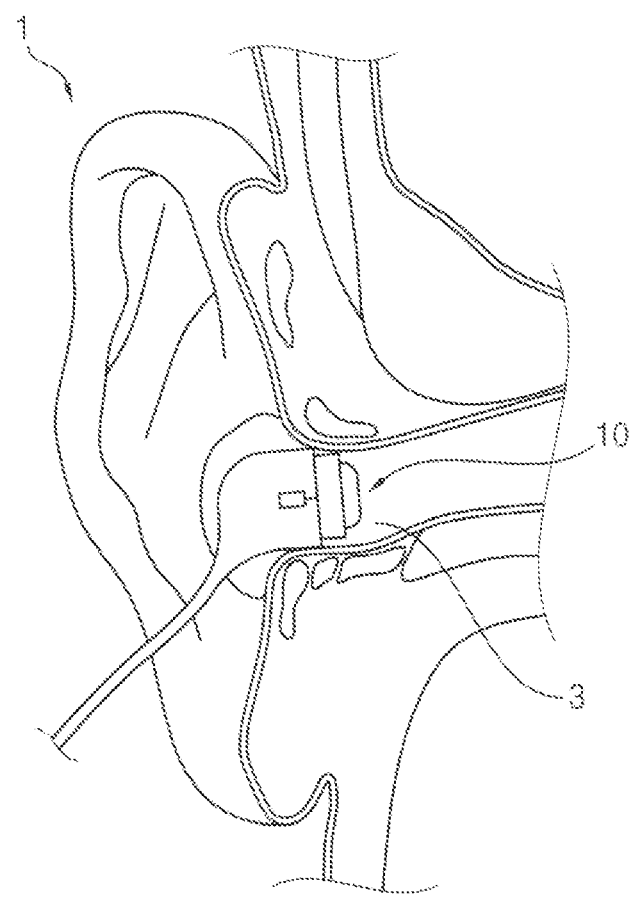
FIG. 1 is a perspective view illustrating a core body temperature measurement device inserted into an ear canal according to an example embodiment of the present invention.

| * Reference numerals | |
|---|---|
| 10: core body temperature measurement device | 100: body |
| 200: front part | 300, 301: operation unit |
| 400: driving part | 500: power |
| 310: cover frame | 320: rotation part |
| 330: first moving part | 340: cover part |
| 350: second moving part | 360: sensor part |
| 370: disinfection part | 390: guide part |
| 391: inner guide | 392: outer guide |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. Spatially relative terms, such as "beneath," "below," "lower," "above," "upper" and the like, may be used herein for ease of description to describe one element or feature's relationship to another element(s) or feature(s) as illustrated in the figures.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms (including technical and scientific terms) used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention is described more fully hereinafter with reference to the accompanying drawings, in which embodiments of the invention are shown.

Figure 2:
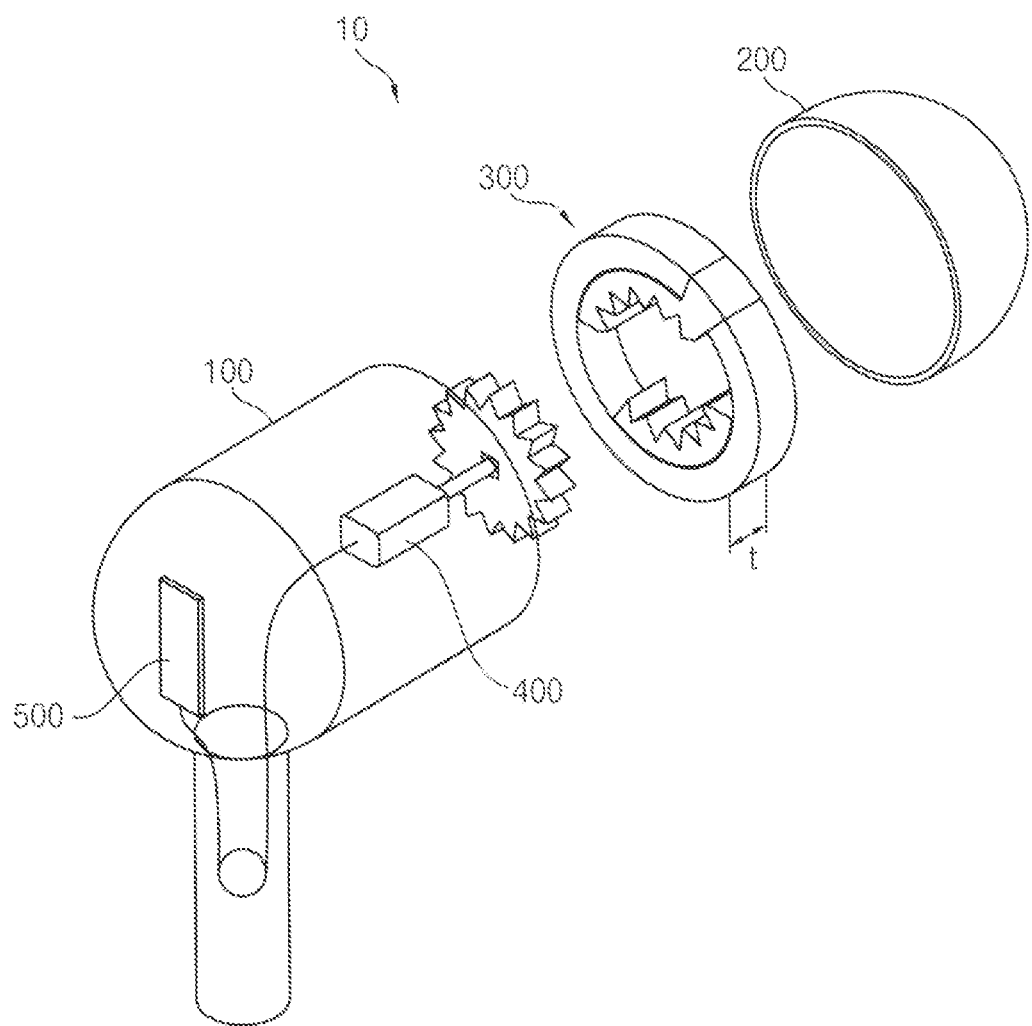
FIG. 2 is an exploded perspective view illustrating the core body temperature measurement device of FIG. 1.
Figure 3A:
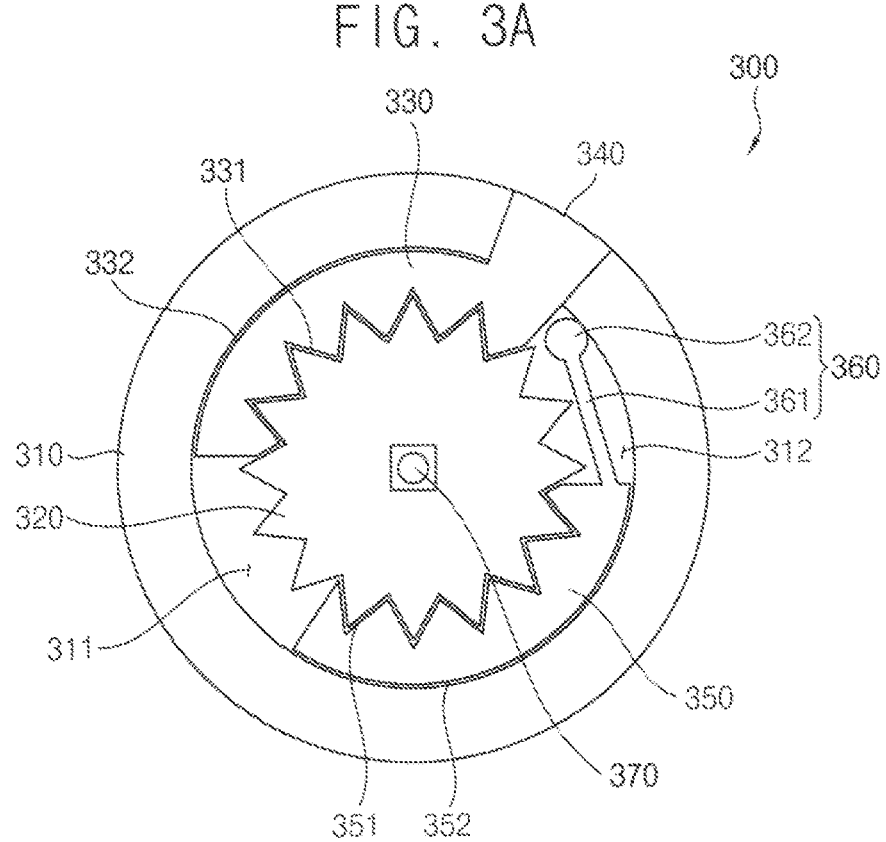
FIG. 3A is a plan view illustrating an operation unit of the core body temperature measurement device of FIG. 1, and FIG. 3B and FIG. 3C are plan views illustrating examples of the operation of the core body temperature measurement device of FIG. 1.
Figure 3B:
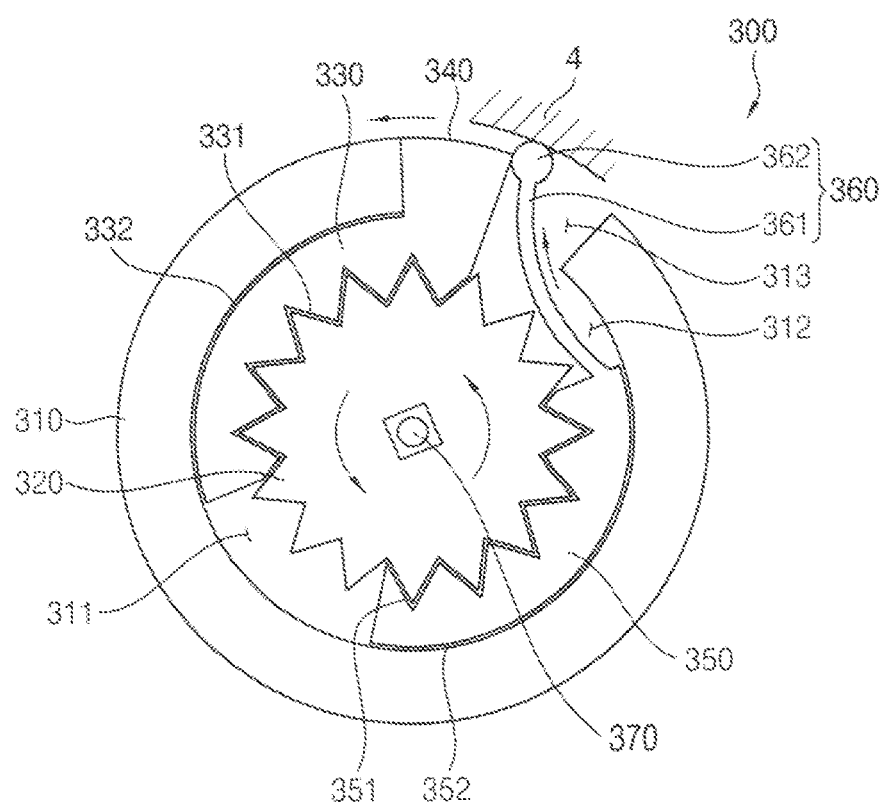

FIG. 1 is a perspective view illustrating a core body temperature measurement device inserted into an ear canal according to an example embodiment of the present invention. FIG. 2 is an exploded perspective view illustrating the core body temperature measurement device of FIG. 1. FIG. 3A is a plan view illustrating an operation unit of the core body temperature measurement device of FIG. 1, and FIG. 3B and FIG. 3C are plan views illustrating examples of the operation of the core body temperature measurement device of FIG. 1.

Figure 3C:
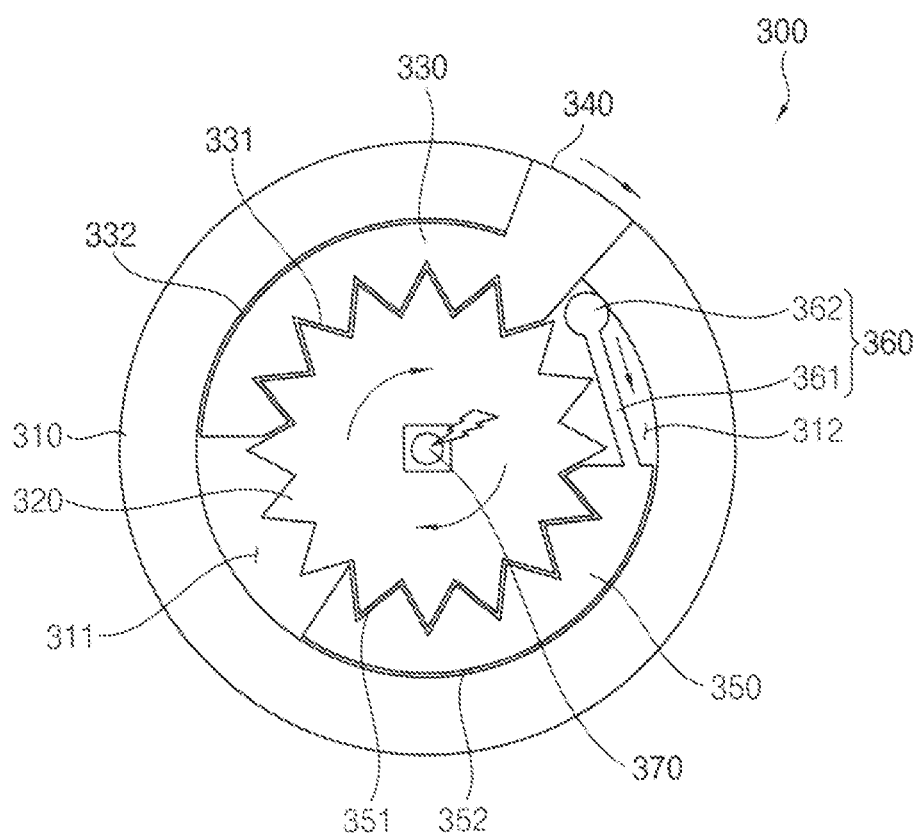

Referring to FIG. 1 and FIG. 3C, the core body temperature measurement device 10, as illustrated in FIG. 1, is inserted into an ear canal 3 of an ear 1 and is fixed to the ear canal 3, for measuring the core body temperature of a user. The core body temperature measurement device 10 includes a body 100, a front part 200, an operation unit 300, a driving part 400 and a power 500.

The body 100 has a shape similar to an ear-phone, and forms a body of the core body temperature measurement device 10. The body 100 is inserted into and fixed to the ear canal 3. The body 100 forms an inner space in which the driving part 400 and the power 500 are received.

Here, the driving part 400 or the power 500 may be received or disposed in the operation unit 300, or in the front part 200 except for the inner space of the body 100. Further, the driving part 400 or the power 500 may be disposed outside of the body, and the position or disposition thereof may be variously changed.

The driving part 400, for example, may be a miniature motor, and the driving part 400 generates the rotational force to provide the rotational force to the operation unit 300.

In addition, the power 500 may provide a power source to the driving part 400.

The operation unit 300 is fixed to a front side of the body 100 and thus is inserted more into the ear canal 3. The front part 200 is additionally fixed to the front side of the operation unit 300, to fix or enclose the operation unit 300.

The thickness of the operation unit 300 may be relatively small, and both sides of the operation unit 300 are enclosed by the body 100 and the front part 200, so that elements inside of the operation unit 300 are blocked from outside.

Accordingly, the core body temperature measurement device 10 according to the present example embodiment, has the shape similar to the conventional shape of the ear-phone, and is inserted into and fixed to the ear canal 3, and then measures the core body temperature.

More specifically, referring to FIG. 3A, the operation unit 300 includes a cover frame 310, a rotation part 320, a first moving part 330, a cover part 340, a second moving part 350, a sensor part 360 and a disinfection part 370.

The cover frame 310 has a ring shape or a circular frame shape forming an inside space, and as illustrated in FIG. 1, the cover frame 310 may have a predetermined thickness 't'.

The rotation part 320, the first and second moving parts 330 and 350, the sensor part 360 and the disinfection part 370 are received in the inside space formed by the cover frame 310. An opening portion 313 is formed at a first side of the cover frame 310, as illustrated in FIG. 3B, and the opening portion 313 is selectively open or closed by the cover part 340.

The rotation part 320 is connected to a driving axis of the driving part 400, and receives the rotational force from the driving part 400. Thus, the rotation part 320 is rotated with respect to a center of the rotation part 320. Here, the rotation part 320 may rotate with a clockwise direction or a counterclockwise direction, and the cover frame 310 is fixed even though the rotation part 320 rotates.

Here, the rotation part 320 rotates with respect to the cover frame 310, inside of the cover frame 310.

Concave portions and convex portions are alternately formed like a gear on an outer circumferential surface of the rotation part 320.

The first moving part 330 is disposed inside of the cover frame 310, and is combined with the rotation part 320. Thus, the first moving part 330 moves due to the rotation of the rotation part 320.

Here, the first moving part 330 includes a first surface 331 and a second surface 332. The first surface 331 is combined with the outer circumferential surface of the rotation part 320 by a gear combination. The second surface 332 faces the first surface 331, makes contact with an inner surface of the cover frame 310 and slidably moves on the inner surface of the cover frame 310.

The first surface 331 may include gear teeth combined with gear teeth formed on the outer circumferential surface of the rotation part 320, to be combined with the outer circumferential surface of the rotation part 320.

Thus, when the rotation part 320 rotates, the first moving part 330 rotates with the same direction of the rotation part 320, and here, the second surface 332 slides on the inner surface of the cover frame along the rotational direction of the rotation part 320.

The cover part 340 is integrally formed with the first moving part 330 at a first side of the first moving part 330, and open or close the opening portion 313 which is formed through the cover frame 310.

As illustrated in FIG. 3A, the cover part 340 encloses the opening part 313 at an initial state. To enclose, a first end of the cover part 340 is fixed to the outer circumferential surface of the rotation part 320, and a second end of the cover part 340 has an area larger than that of the opening portion 313 to entirely enclose the opening portion 313.

In addition, as illustrated in FIG. 3B, the cover part 340 moves with the first moving part 330 according to the rotation of the rotation part 320, and thus the cover part 340 is open. Although not shown in detail in the figure, to open the opening portion 313 due to the movement of the cover part 340, an additional space in which the cover part 340 is disposed may be formed in the cover frame 310.

The second moving part 350 is disposed inside of the cover frame 310 like the first moving part 330. The second moving part 350 is combined with the rotation part 320 and rotates due to the rotation of the rotation part 320.

Here, the second moving part 350 is disposed at an opposite side of the first moving part, and thus the first and second moving parts 330 and 350 face each other.

The second moving part 350 includes a first surface 351 and a second surface 352. The first surface 351 is combined with the outer circumferential surface of the rotation part 320 by a gear combination. The second surface 352 faces the first surface 351, makes contact with the inner surface of the cover frame 310 and slidably moves on the inner surface of the cover frame 310.

The first surface 351 may include gear teeth combined with gear teeth formed on the outer circumferential surface of the rotation part 320, to be combined with the outer circumferential surface of the rotation part 320.

Thus, when the rotation part 320 rotates, the second moving part 350 rotates with the same direction of the rotation part 320, and here, the second surface 352 slides on the inner surface of the cover frame 310 along the rotational direction of the rotation part 320.

Accordingly, the rotation part 320, and the first and second moving parts 330 and 350 are received inside of the cover frame 310, and here, the first and second moving parts 330 and 350 are spaced apart and do not make contact with each other. Thus, a first space 311 and a second space 312 are formed inside of the cover frame 310.

As the rotation part 320 rotates, the first and second spaces 311 and 312 moves along the movements of the first and second moving parts 330 and 350.

The sensor part 360 is disposed in the second space 312 in which the opening portion 313 is formed. Here, the sensor part 360 includes an extending portion 361 and a sensor 362.

A first end of the extending portion 361 is fixed to an end surface of the second moving part 350, and the extending portion 361 extends toward the cover part 340 or the opening portion 313.

The sensor 362 is formed at a second end of the extending portion 361, and for example, may be a thermistor measuring a body temperature.

Accordingly, as the senor part 360 is fixed to the second moving part 350, and thus as the second moving part 350 moves, the sensor part 360 also moves.

The disinfection part 370, as illustrated in FIG. 3A, is disposed at a center of the rotation part 320, but alternatively, the disinfection part 370 may be disposed at any position inside of the cover frame 310, capable of disinfecting the sensor part 360.

The disinfection part 370 generates a light to disinfect the sensor part 360, specifically the sensor 362, and the light from the disinfection part 370 may be, for example, UV LED capable of sterilizing.

Although not shown in the figure, the disinfection part 370 may be connected to an additional power source and may be ON or OFF by the operation of the power source. Alternatively, the disinfection part 370 is linked with the rotation part 320, and thus may be ON or OFF according to a rotational direction of the rotation part 320.

Here, as the rotation part 320 starts to rotate along the counterclockwise direction, the disinfection part 370 may be OFF, and as the rotation part 320 starts to rotate along the clockwise direction, the disinfection part 370 may be ON.

The disinfection part 370 generates the light for the sterilization, and thus the light generated from the disinfection part 370 should be blocked from being provided to the ear canal 3 of the user by the cover frame 310. Thus, the above ON and OFF control for the disinfection part 370 is necessary, since the opening portion 313 is operated with covered by the cover part 340.

Alternatively, the disinfection part 370 may be manually controlled by the user, and here, the disinfection part 370 should be operated with the opening portion 313 closed or covered as mentioned above.

In the present example embodiment, an example in which the sensor part 360 is fixed to the second moving part 350, which means that the single sensor part 360 is equipped, is explained, but alternatively, a pair of sensor parts 360 may be equipped.

That is, the sensor part 360 may be disposed both in the second space 312 and the first space 311. Here, the opening portion 313 explained above may be also formed at an opposite side symmetrically, and the cover part 340 may be formed to enclose the opening portion at the symmetric position and the cover part 340 should be connected and fixed to the second moving part 350. In addition, the additional sensor part may be connected to the first moving part 330 and may be disposed in the first space 311.

Thus, as the rotation part 320 rotates along the counterclockwise direction or the clockwise direction, the pair of sensor parts may be respectively exposed through the opening portions formed at the opposite sides at the same time, and may be concealed inside of the opening portions at the same time., Hereinafter, referring to FIG. 3A, FIG. 3B and FIG. 3C, the operation of the operation unit 300 is explained.

First, referring to FIG. 3A, at the initial state, the opening portion 313 of the cover frame 310 is enclosed by the cover part 340, and the sensor part 360 fixed to the second moving part 350 is disposed in the second space 312.

Then, referring to FIG. 3b, as the rotation part 320 rotates along the counterclockwise direction, the first and second moving parts 330 and 350 combined with the gear teeth of the rotation part 320 also rotates along the counterclockwise direction.

Accordingly, the cover part 340 fixed to the first moving part 330 also moves along the counterclockwise direction, and thus the opening portion 313 is open.

Here, the sensor part 360 fixed to the second moving part 350 also moves along the counterclockwise direction, and the extending portion 361 is curved and the extending direction of the extending portion 361 is changed due to the cover part 340. Then, the sensor 362 is protruded into the opening portion 313.

Here, the extending portion 361 may include a flexible or elastic material, and thus the moving or extending direction of the extending portion 361 may be changed by the cover part 340.

Accordingly, as the sensor 362 passes through the opening portion 313 to be protruded to outside, the sensor 362 makes contact with or becomes closer to a skin 4 of the ear canal 3 to measure the core body temperature of the user.

Then, referring to FIG. 3C, after the measurement for the core body temperature is completed, the rotation part 320 rotates along the clockwise direction, and thus the first and second moving parts 330 and 350 combined with the gear teeth of the rotation part 320 also move along the clockwise direction.

Then, the cover part 340 fixed to the first moving part 330 also moves along the clockwise direction, to enclose the opening portion 313.

Here, the sensor part 360 fixed to the second moving part 350 also moves along the clockwise direction, and thus the sensor part 360 is positioned inside of the second space 312.

Accordingly, as the sensor part 360 is positioned inside of the second space 312, the disinfection part 370 is automatically or manually operated, to sterilize the sensor part 360.

Then, if the measurement for the core body temperature is necessary again, the above-mentioned operations are repeated.

Figure 4A:
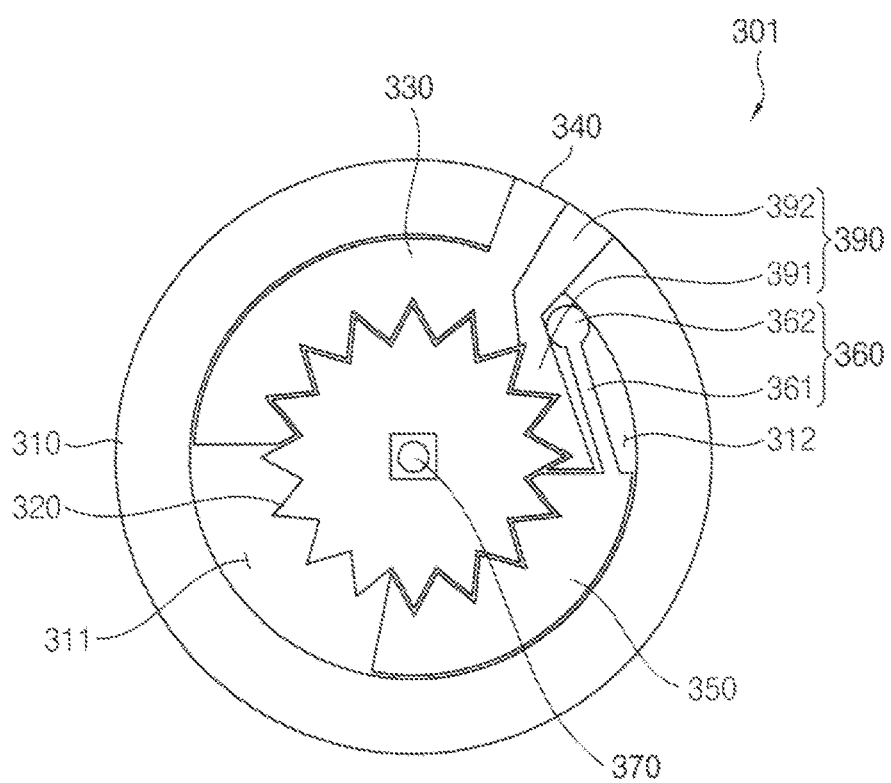
FIG. 4A and FIG. 4B are plan views illustrating an operation unit and an operation state of a core body temperature measurement device according to another example embodiment of the present invention.
Figure 4B:
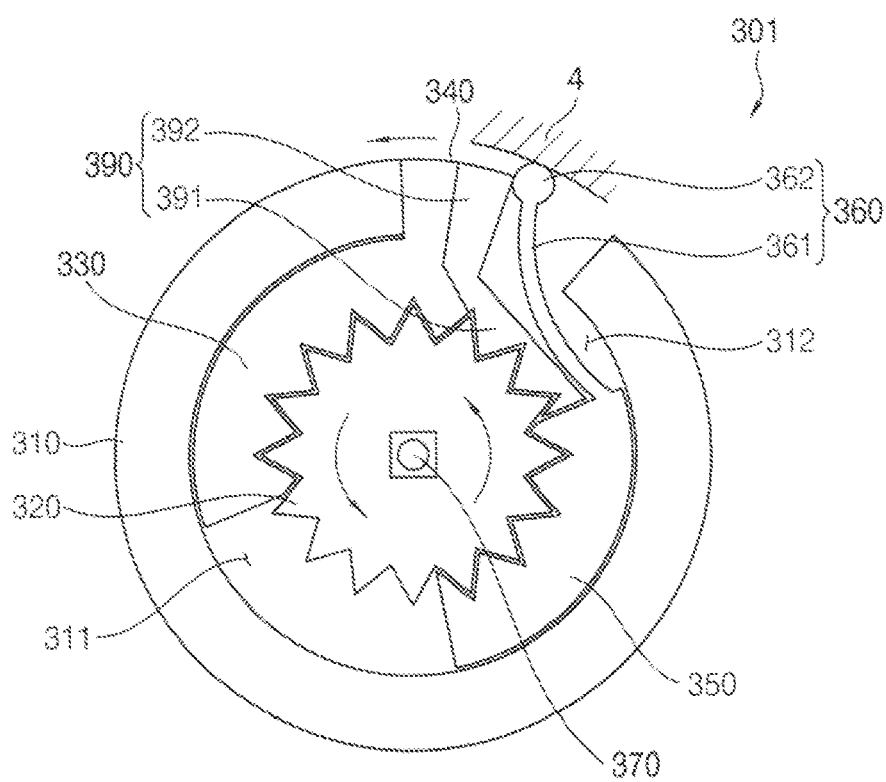

FIG. 4A and FIG. 4B are plan views illustrating an operation unit and an operation state of a core body temperature measurement device according to another example embodiment of the present invention.

The core body temperature measurement device according to the present example embodiment is substantially same as the core body temperature measurement device according to the previous example embodiment, except that an operation unit 301 further includes a guide part 390, and thus same reference numerals are used for the same elements and any repetitive explanation will be omitted.

Referring to FIG. 4A and FIG. 4B, in the present example embodiment, the operation unit 301 further includes the guide part 390.

The guide part 390 may be combined with the cover part 340, or may be integrally formed with the cover part 340, to guide the movement of the sensor part 360.

The guide part 390, as illustrated in the figure, includes an inner guide 391 and an outer guide 392 integrally formed with each other. A first end of the inner guide 391 is combined with and fixed to the rotation part 320 via a gear combination, and a second end of the outer guide 392 is exposed to outside and selectively opens or closes the opening portion 313 with the cover part 340.

Here, the guide part 390, as illustrated in FIG. 4A, a curved portion is formed between the inner guide 391 and the outer guide 392, and thus the sensor 362 is disposed on the curved portion when the sensor part 360 is received in the second space 312.

Thus, the sensor 362 is prevented from being impacted to the rotation part 320 or the cover frame 310 since the position of the sensor 362 is fixed in the second space 312, and thus the sensor 362 is prevented from being damaged.

In addition, when the sensor 362 of the sensor part 360 is exposed outside, the outer guide 392 forms a moving guide to control the protruded direction of the sensor 362. The outer guide 392 includes an inclined surface, and thus the sensor 362 is exposed outside through the opening portion 313 along the inclined surface.

Accordingly, the guide part 390, in the present example embodiment, solves the problem that the sensor 362 is exposed along an unintended direction and thus the sensor 362 is not exposed toward the skin 4 of the ear canal 3, and thus the sensor 362 may be positioned at an optimized position for the core body temperature measurement.

According to the present example embodiments, the sensor part is selectively exposed to the ear canal or is concealed inside, and the core-temperature is measured when exposed, and thus the sensor may be prevented from being infected or the user may feel less inconvenience or less foreign body since the sensor part is not always disposed in the ear canal.

An operation structure or motion for exposing or concealing the sensor part, is merely performed by the clockwise or counterclockwise rotation of the rotation part, and thus the operation structure or motion is very simple, so that the sensor part may be easily driven in a relatively narrow space of the ear canal. Thus, usability and productivity may be increased.

Here, the first and second moving parts are combined with the rotation part via a gear combination, so that the operation may be stably controlled with a stable combination state.

The cover frame is closed or open by the cover part, and at the same time, the exposure of the sensor part through the opening portion is performed with the movement of the cover frame, so that the control and the driving may be more simplified.

In addition, the sensor part is guided by the guide part, so that the exposure and the concealment of the sensor part may be performed with more increased reliability.

In addition, the sensor part is disinfected by the disinfection part when the sensor part is concealed, so that the sensor part which is disposed at the ear canal to be easily infected is prevented from being infected. Further, during the disinfection, the noxious light or material is prevented from being exposed to the user by the cover frame, so that the sensor part may be maintained more cleanly and may measure the core body temperature more correctly.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A core body temperature measurement device comprising:
   a body configured to be fixed to an ear canal of a user; and
   an operation unit combined with a front side of the body, and having a sensor part,
   wherein the sensor part measures a core body temperature of the user when the operation unit is exposed to the ear canal,
   wherein the operation unit comprises:
   a cover frame configured to form an outer shape of the operation unit;
   a rotation part disposed inside of the cover frame, and configured to be rotated upon application of a driving force thereon; and
   a moving part comprising a first moving part that is combined to one half of the rotation part and a second moving part that is combined to an other half of the rotation part and configured to move along an inner side of the cover frame when the rotation part is rotated,
   wherein the sensor part is fixed to the second moving part, and
   wherein the sensor part is exposed outside of the cover frame to measure the core body temperature, and is selectively concealed inside of the cover frame, according to the movement of the second moving part.

2. The device of claim 1, wherein the operation unit further comprises:
   a disinfection part configured to disinfect the sensor part, when the sensor part is concealed inside of the cover frame.

3. The device of claim 1, wherein the sensor part comprises:
   an extending portion fixed to the second moving part and extending along a direction; and
   a sensor disposed at an end of the extending portion, to measure the core body temperature.

4. The device of claim 3, wherein the operation unit comprises:
   a cover part fixed to the first moving part, and configured to open or close an opening portion of the cover frame through which the sensor part is exposed.

5. The device of claim 4, wherein the operation unit further comprises a guide part,
   wherein the guide part is attached with the cover part and a first end of the guide part is combined with the rotation part, to open or close the opening portion of the cover frame with the cover part, and
   wherein the guide part forms a guide in which the sensor part moves.

* * * * *